US008627724B2

(12) United States Patent
Papadopoulos et al.

(10) Patent No.: US 8,627,724 B2
(45) Date of Patent: Jan. 14, 2014

(54) NON-INTRUSIVE SENSOR FOR IN-SITU MEASUREMENT OF RECESSION RATE OF ABLATIVE AND ERODING MATERIALS

(75) Inventors: George Papadopoulos, Nesconset, NY (US); Nicholas Tiliakos, Huntington Station, NY (US); Gabriel Benel, New York, NY (US); Clint Thomson, Smithfield, UT (US)

(73) Assignee: Alliant Techsystems Inc., Minneapolis, MN (US)

( * ) Notice: Subject to any disclaimer, the term of this patent is extended or adjusted under 35 U.S.C. 154(b) by 265 days.

(21) Appl. No.: 13/224,214

(22) Filed: Sep. 1, 2011

(65) Prior Publication Data
US 2012/0085173 A1 Apr. 12, 2012

Related U.S. Application Data

(60) Provisional application No. 61/379,463, filed on Sep. 2, 2010.

(51) Int. Cl.
*G01N 29/07* (2006.01)
(52) U.S. Cl.
USPC .................................. 73/598; 73/602; 73/622
(58) Field of Classification Search
USPC ............ 73/598, 504.02, 504.04, 504.13, 602, 73/622, 637, 638
See application file for complete search history.

(56) References Cited

U.S. PATENT DOCUMENTS

| | | | | |
|---|---|---|---|---|
| 4,073,193 A | * | 2/1978 | Mastandrea | 73/865.5 |
| 5,056,367 A | * | 10/1991 | Marshall | 73/597 |
| 5,251,487 A | * | 10/1993 | Marshall | 73/644 |
| 5,421,206 A | * | 6/1995 | Rohwedder | 73/834 |
| 7,637,157 B2 | * | 12/2009 | Chikovani et al. | 73/504.13 |

* cited by examiner

*Primary Examiner* — J M Saint Surin
(74) *Attorney, Agent, or Firm* — Vidas, Arrett & Steinkraus, P.A.

(57) ABSTRACT

A non-intrusive sensor for in-situ measurement of recession rate of heat shield ablatives. An ultrasonic wave source is carried in the housing. A microphone is also carried in the housing, for collecting the reflected ultrasonic waves from an interface surface of the ablative material. A time phasing control circuit is also included for time-phasing the ultrasonic wave source so that the waves reflected from the interface surface of the ablative material focus on the microphone, to maximize the acoustic pressure detected by the microphone and to mitigate acoustic velocity variation effects through the material through a de-coupling process that involves a software algorithm. A software circuit for computing the location off of which the ultrasonic waves scattered to focus back at the microphone is also included, so that the recession rate of the heat shield ablative may be monitored in real-time through the scan-focus approach.

19 Claims, 16 Drawing Sheets

NON-INTRUSIVE SENSOR FOR IN-SITU MEASUREMENT OF RECESSION RATE OF ABLATIVE AND ERODING MATERIALS

CROSS-REFERENCE TO RELATED APPLICATIONS

This application claims priority from provisional application No. 61/379,463, filed Sep. 2, 2010, the entire contents of which is hereby incorporated by reference.

STATEMENT REGARDING FEDERALLY SPONSORED RESEARCH

The invention herein claimed was made in the course of or under a contract with NASA Ames Research Center, Contract Number NNA08BA27C.

FIELD OF THE INVENTION

The invention relates to a new sensor for in-situ non-intrusive measurements of recession rate of ablative and eroding materials. In particular, the sensor utilizes a focused ultrasound approach to non-intrusively detect the material's surface loss while simultaneously correcting for acoustic velocity dependencies on material properties and characteristics, such as temperature, density, etc. The invention was conceived to address specifically recession rate of heat shield ablatives, but it could be utilized in the same manner in other applications where the recession rate of a material needs to be measured in-situ.

BACKGROUND OF THE INVENTION

Thermal protection systems (TPS) are critical towards making hypersonic flight a reality, as well as, ensuring that future spacecraft will have the capabilities needed to descent through the Martian or other planet atmosphere. There are various passive and active methods of cooling the skin of a vehicle, as well as novel materials, which include CMC's, refractory metals, and ablatives. Regarding ablation technology, having a device that can measure ablation recession rate for real-time, in-flight sensing is highly desirable as progress is made to increasingly prove-out hypersonic technologies through ground testing and eventually flight testing. Such a recession rate sensor would be an important part of an entire sensor suite that helps monitor the structural health of future hypersonic flight vehicles, which of course include both earth based high speed air breathers and spacecraft modules destined for use in NASA's mission to land on Mars and beyond.

Various researchers have investigated different approaches to measuring TPS recession rates that have involved inserting breakwires into the ablative (1Hycal Engineering, "In-Depth Ablative Plug Transducers," Series #S-2835, 9650, 1992, Telstar Avenue, P.O. Box 5488, El Monte, Calif.), implanting quartz fibers terminating at known depths into the ablator (Legendre, P. J., "Reentry Vehicle Nosetip Instrumentation," *Proceedings of the 22nd International Instrumentation Symposium*, San Diego, Calif., 1975.), or embedding a ladder or continuous configuration of resistive elements (Gramer, D. J., Taagen, T. J., and Vermaak, A. G., "Embedded Sensors for Measuring Surface Regression," *NASA Tech Briefs*, July 2006.). Another approach employs a capacitive sensor placed in series with an inductor and resistor to form an RLC terminator to a waveguide (4Noffz, G. K., and Bowman, M. P., "Design and Laboratory Validation of a Capacitive Sensor for Measuring the Recession of a Thin-Layered Ablator," NASA Technical Memorandum 4777, 1996.). This approach is dependent on the material's dielectric properties and may not be applicable for all ablative materials. The entire contents of each of the references discussed above is hereby incorporated by reference.

Current state of the art technology for measuring ablation rate sensors involve approaches that:

are intrusive, thereby affecting the ablator's integrity and requiring the embedded sensor to withstand extremely high temperatures;

rely on sensing changes in ablator material properties, (e.g. sound speed) to detect a recession rate and are therefore sensitive to temperature effects on these same properties;

have relatively poor resolution, thus making it difficult to measure the ablation rate of relatively thinner TPS systems found on booster vehicles.

cannot survive the high temperature environment.

are not conducive for flight applications, with bulky hardware and complex electronics.

There is no practical sensor technology currently in use to measure the recession of an ablative material in-situ and in-flight. The closest is the implementation of breakwires into the ablative as discrete indicators of recession. However, this is an intrusive method, and the desire is strong to have a non-intrusive method developed so that the ablative material is not compromised in any way.

BRIEF SUMMARY OF THE INVENTION

A non-intrusive sensor for in-situ measurement of recession rate of heat shield ablatives and other eroding materials, comprising a housing, which can be mounted near a material for which the recession rate is to be monitored. An ultrasonic wave source is carried in the housing. A microphone is also carried in the housing, for collecting the reflected ultrasonic waves from an interface surface of the ablative material. A time phasing control circuit is also included for time-phasing the ultrasonic wave source so that the waves reflected from the interface surface of the ablative material focus on the microphone, to maximize the acoustic pressure detected by the microphone and to mitigate acoustic velocity variation effects through the material through a de-coupling process that involves a software algorithm. A software circuit for computing the location off of which the ultrasonic waves scattered to focus back at the microphone is also included, so that the recession rate of the heat shield ablative may be monitored in real-time through the scan-focus approach.

DETAILED DESCRIPTION OF THE INVENTION

Figure 1:
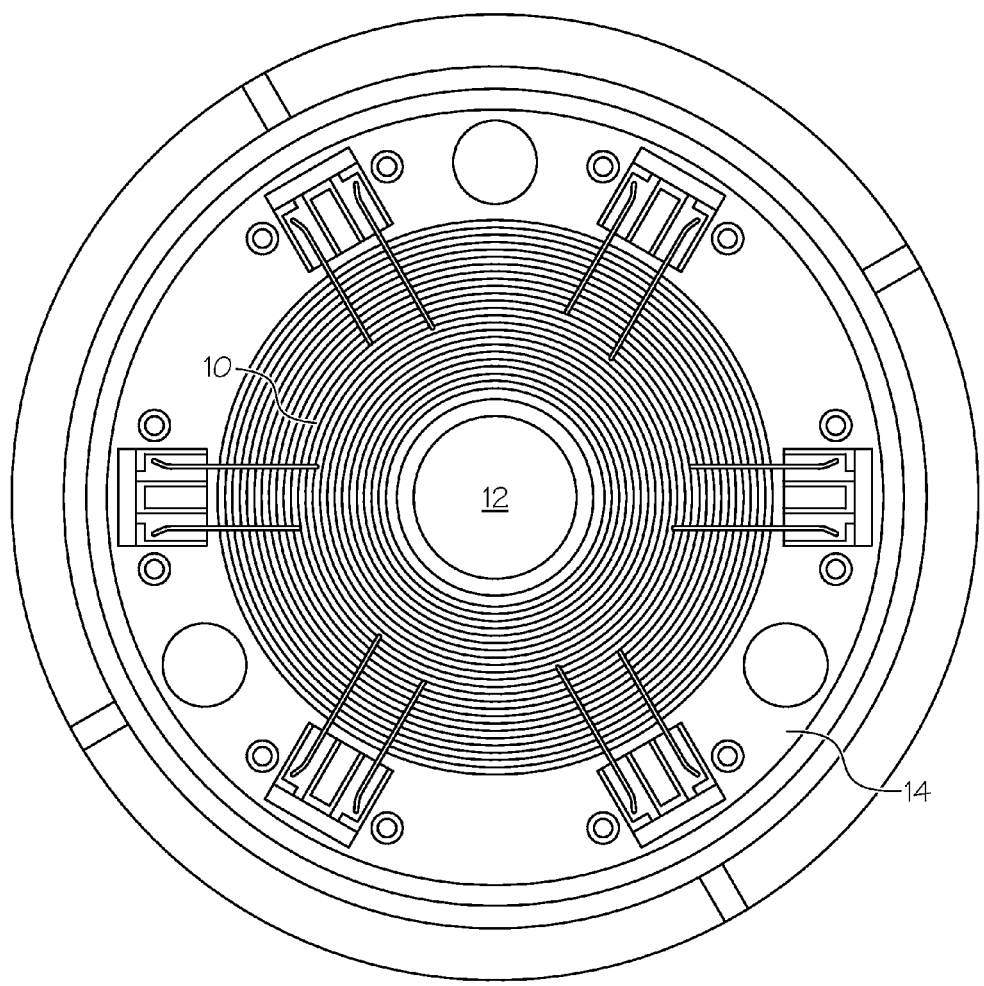
FIG. 1 is a view of the sensor hardware showing a concentric piezoelectric ring arrangement with a center microphone.

While this invention may be embodied in many forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

The following nomenclature is used in this application:
C=acoustic velocity (function of material properties)
$C_0$=reference acoustic velocity
$C_{int}$=acoustic velocity at ablator's hot interface
i=ring index
r=radial distance outward from sensor center
t=time
T=temperature
$T_0$=reference temperature (or sensor side temperature of ablator)
$T_{int}$=temperature at ablator's hot interface
z=height of material (normal to sensor plane)=
δτ=transit time differential due to geometric effects
∈τ=transit time differential due to acoustic velocity variants within material
τ=total transit time The invention is a novel approach in using ultrasonic's for non-intrusively probing the ablating or eroding material to generate information on the top surface recession rate. Ultrasonic transducer technology has been used to measure recession rates of ablative materials by determining the time of flight of sound waves in a typical pulse-echo setup scenario where the sound waves reflect back from the interface. However, transit time of sound waves is strongly affected by the structural characteristics of the material, which in turn are strongly affected by temperature in the case of heat shield material. Thus, inaccurate determination of the distance to the interface results from not knowing the temperature distribution correctly. Certain assumptions and empirical trends need to be deployed to post-process the transit time measurements and correct for the temperature effect on the acoustic velocity.

Clearly, such an approach that utilizes a-priori knowledge of the temperature distribution from assumed trends has severe limitations when applied to nonisotropic materials and atypical heating scenarios. Furthermore, determining changes in transit time to resolve small changes or for application to thin materials requires highly fast and resolved data acquisition equipment that makes sensor miniaturization challenging.

A goal with the current recession rate sensor invention was to preserve the benefit of non-intrusiveness that ultrasound offers but mitigate against the need of a-priori knowledge of the heating rates by considering a novel multi-source, focusing approach that can simultaneously yield the real-time interface location and acoustic velocity variation needed for correction. Furthermore, a hybrid approach to interface localization was used to improve reliability, baseline transit time calculation and maximization of acoustic pressure through focusing. Lastly, while typical ultrasonic measurements require operation at high frequencies (MHz) to yield well resolved measurements, the current focusing principle approach can be utilized equally with a broad array of ultrasonic elements operating at frequencies in the KHz to MHz range, with operation in the low frequency range a must if penetration into highly porous ablative materials is to be achieved.

The motivation of the current research effort was to develop a sensor system for ablation recession rate measurement with the following benefits and features:

Non-intrusiveness: can be surface mounted, without compromising the structural integrity of composite structures, and the ablative material;

Real-time monitoring: capable of real-time tracking of material recession rates, with a typical response rate in 10 s of Hz, or better;

Compact Design: can be packaged in low-profile, small footprint, lightweight housing with associated hard-wired electronics for in-situ operation;

Robust: capable of withstanding structural vibration and mechanical shocks, can be placed in locations where it is not in direct contact with the ablative material surface to avoid thermal issues, and adaptable in operating frequency to mitigate against adverse material properties that limit high frequency ultrasonic wave propagation;

Auto Temperature Compensating: capable of determining the average acoustic velocity through the ablative material needed for compensating temperature effects and yielding correct measurement of recession rate Referring now to FIG. 1, the inventive sensor departs from the traditional single ultrasonic sensor approach by utilizing an annular concentric array of resonators as the ultrasonic wave source and an independent microphone in the center for reflective wave collection. Shown in the figure is the breadboard sensor device, which featured 12 piezoelectric rings 10 and a center microphone 12. The rings are attached on the underside of a copper backing 14, which incorporates filler material to mitigate against back resonance. Electrical connections consisted of insulated wiring bonded to the top of each ring terminating into a coupler, as seen in the figure. A quartz wear plate was placed on top sealing the piezoelectric rings from the environment with RTV vacuum grease serving as the coupler material to the ablative.

The sensor was operated by time-phasing the rings so that their waves focus at various locations within the material after reflecting off the interface. Acoustic pressure at the microphone was monitored during this process. When the waves were time-phased so that they all focused back at the microphone, maximum pressure was observed. Simple geometric algebra then yielded the interface location off of which the waves scattered to focus back at the microphone. This method did not rely on transit time information, and thus did not need sophisticated data acquisition and data processing algorithms.

Figure 2:
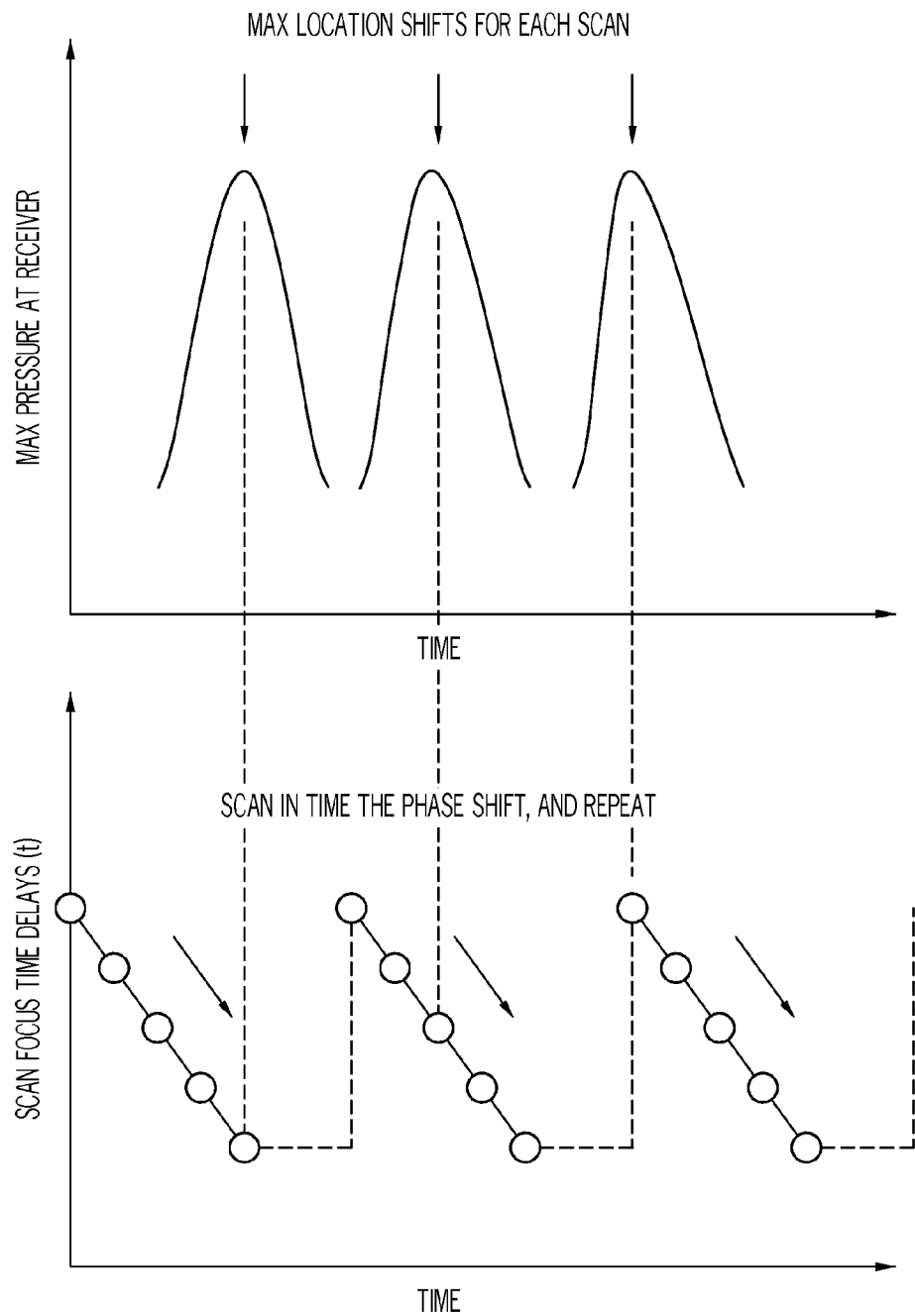
FIG. 2 is a view of the scan-focus approach to identify the interface location based on maximum pressure signal at receiver.

A schematic of the scan-focus approach is shown in FIG. 2. As the interface location receded, the location of the peak based on the scan-focus method also moved. Local peak fitting of the pressure signal resulted in a resolved measurement of the peak location, and thus the interface location. During preliminary testing of the sensor, however, it was decided to implement the classical transit time approach on top of this scan-focusing approach to yield increased resolution for interface localization. Therefore, the ultimate solution was a hybrid approach.

Figure 3:
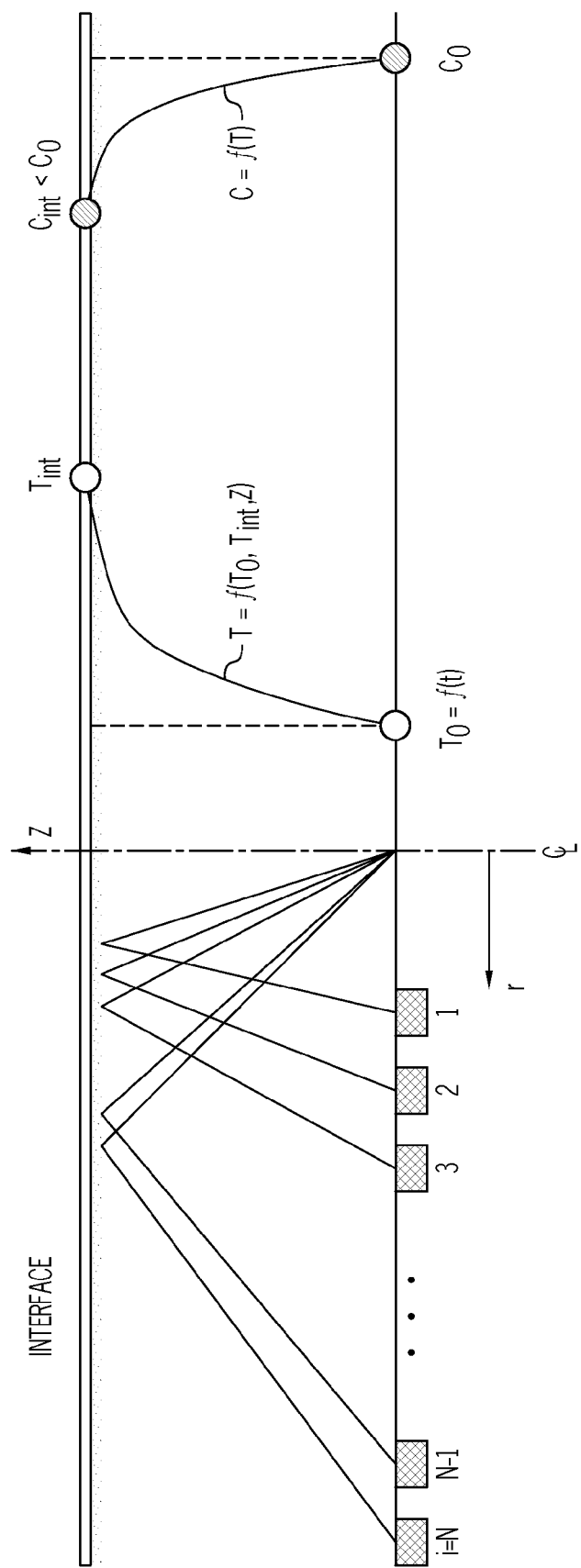
FIG. 3 is a view of a wave propagation and focusing model along with notional distributions of temperature and acoustic velocity for ablative material.

The aforementioned process is straight forward when the acoustic velocity within the material is known and does not change. However, when the acoustic velocity is changing due to temperature, the pressure response curve measured by the microphone will be affected in both magnitude and shape. As illustrated in FIG. 3, each PZT ring sends out an acoustic wave that will reflect off the interface location some vertical distance z and then focus at the center of the sensor where the microphone is located. For simplicity, aperture affects on the return signal are neglected. Focusing brings all waves emanating from all N number of rings in phase at r=0 and z=0. Therefore, the total transit time is the same for each wave, which can be expressed as:

$$\tau_i = \frac{2}{C_o}\left(\frac{r_i^2}{4} + z_0^2\right)^{\frac{1}{2}} (\text{ring } i) \quad \text{Equation 1}$$

$$\tau_{i+1} = \frac{2}{C_o}\left(\frac{r_{i+1}^2}{4} + z_0^2\right)^{\frac{1}{2}} = \tau_i + \delta\tau_{i+1:i} (adjacent ring)$$

where $\delta\tau_{i+1:i}$ is the time shift of the adjacent ring performed by the electronics based on geometric considerations given ring and interface locations, and also assuming a constant acoustic velocity through the material of $C_0$. Note that sequencing of the rings starts from the outer ring first and ends with the most inner last.

If the acoustic velocity through the material is variable due to heating, then we have:

$$\tau_i = \frac{2}{C(T)}\left(\frac{r_i^2}{4} + z_0^2\right)^{\frac{1}{2}} = \frac{1}{C(T)}\sqrt{r_i^2 + 4z_0^2} (\text{ring } i) \quad \text{Equation 2}$$

$$\tau_{i+1} = \frac{1}{C(T)}\sqrt{r_{i+1}^2 + 4z_0^2} = \tau_i + \delta\tau_{i+1:i} + \varepsilon\tau_{i+1:i}$$

(adjacent ring)

where the additional term of $\varepsilon\tau_{i+1:i}$ is the time shift required to correct for the differential effect on transit time due to path-specific acoustic velocity variation. Given an acoustic velocity distribution within the material that varies along the z direction, then since each resonator is discretely displaced from each other, the path of the respective waves from each resonator to the microphone will be slightly different. Given that, the integral effect due to acoustic velocity will result in the need to make the fine adjustment in time that is noted as $\varepsilon\tau_{i+1:i}$. If we know C(T) then we can determine $\varepsilon\tau_{i+1:i}$. Conversely, if we electronically tune each resonator to compensate for $\varepsilon\tau_{i+1:i}$, then we in effect compensate for integral effect of C(T).

Therefore, the inventive approach for auto-compensation of temperature effects on material properties is to perform real-time tuning of the time-shift parameters of each ring through a feedback mechanism so that the response curve is maximized, thus returned back to its original shape for that particular interface location. The variation in acoustic velocity puts the waves reflecting back to the microphone out of phase with each other and thus degrades signal magnitude. The additional real-time electronic tuning compensates for that.

The algorithm for acoustic velocity compensation goes as:

$$\left\{\begin{array}{c} t_1 + \delta\tau_1 \\ t_2 + \delta\tau_2 \\ \vdots \\ t_{N-1} + \delta\tau_{N-1} \\ t_N + \delta\tau_N \end{array}\right\}^{\langle s-1\rangle} + \left\{\begin{array}{c} \varepsilon\tau_1 \\ \varepsilon\tau_2 \\ \vdots \\ \varepsilon\tau_{N-1} \\ \varepsilon\tau_N \end{array}\right\}^{\langle s\rangle} =$$

$$\frac{1}{N}\left\{\begin{array}{c} D_1 \\ D_2 \\ \vdots \\ D_{N-1} \\ D_N \end{array}\right\}^{\langle s-1\rangle} \otimes \left\{\begin{array}{ccccc} \frac{1}{C_1} & \frac{1}{C_2} & \cdots & \frac{1}{C_{N-1}} & \frac{1}{C_N} \end{array}\right\}^{\langle s\rangle} =$$

$$\left\{\begin{array}{c} D_1 \\ D_2 \\ \vdots \\ D_{N-1} \\ D_N \end{array}\right\}^{\langle s-1\rangle} \cdot \frac{1}{C_{avg}^{\langle s\rangle}}$$

where <s−1> denotes prior time step; <s> denotes current time step. The left hand side is known, with ET terms representing the adjustment that needs to be made due to the change in acoustic velocity over and above the adjustment that was made to locate the interface in the prior scan.

It is assumed that the interface location, z, is frozen while the time shifts are optimized in search of the peak value.

This yields an epsilon on τ that can be used to adjust the time-of-flight values of the prior time step.

From the equation, it is found however, that since the ET terms are due to the acoustic velocity change effect on the integrated path, individual zonal information is lost, and ET is tied to the average acoustic velocity within the material, Cavg.

FIG. 1 shows a view of an embodiment the sensor hardware. Twelve rings 10 of PZT 5H material made up the resonators. The rings 10 were 0.020 inches (0.508 mm) wide by 0.044 inches (1.118 mm) thick, and were concentrically placed at a separation distance of approximately one ring width. The center microphone 12 was an Olympus C106, piezoelectric based, with a frequency response curve centered around 2.25 MHz. It should be understood that other frequencies can also be used. The frequency will be optimized depending on the material acoustic wave propagation properties.

Figure 4:
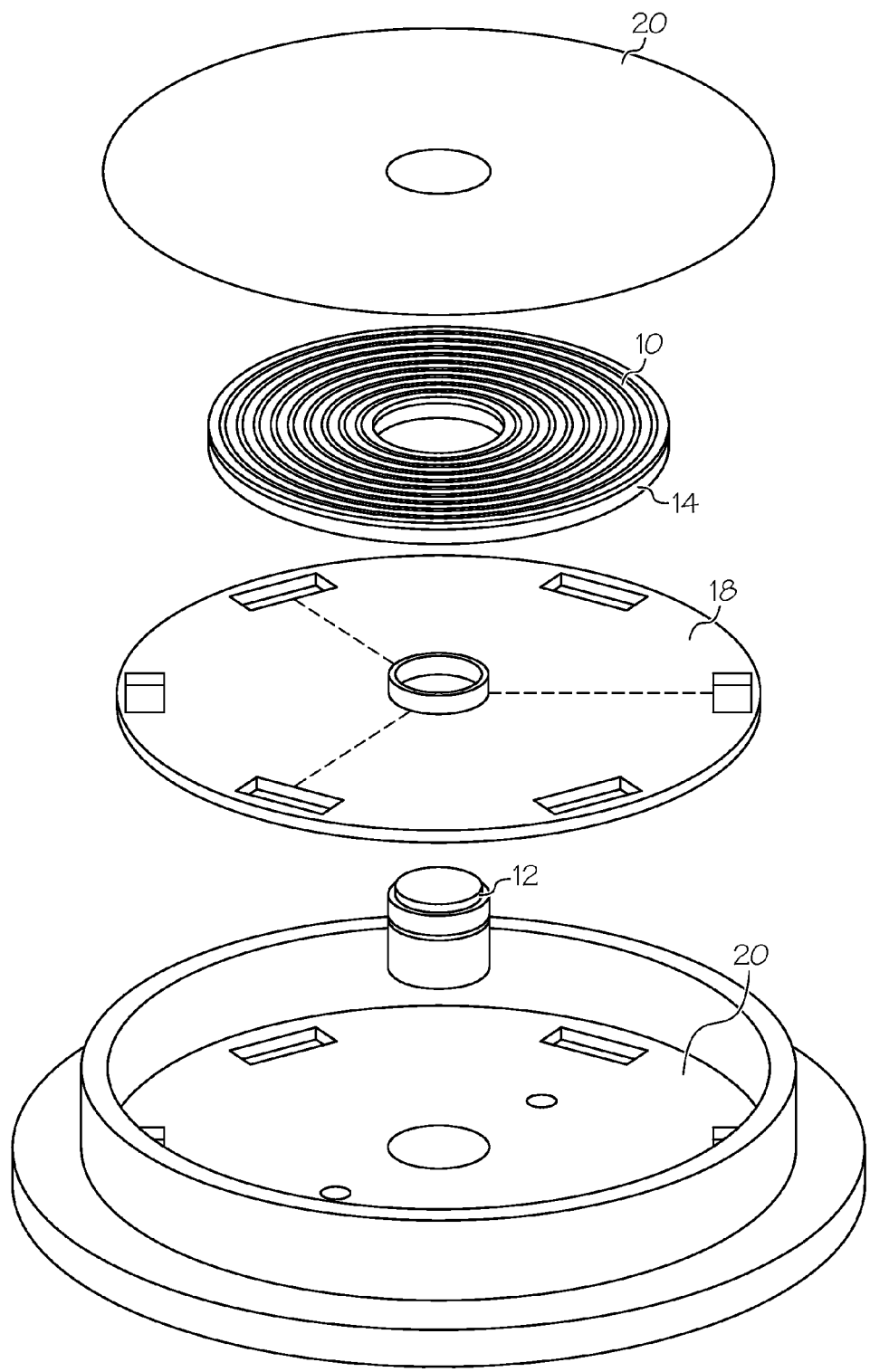
FIG. 4 is an assembly view of the inventive sensor.

An exploded view of the sensor assembly is shown in FIG. 4. The housing is shown at 16. The microphone is shown at 12. The ring holder is shown at 18 with electrical connector cut-outs. The piezo rings are shown at 10, with the metal carrier backing shown at 14. The quartz wear plate is shown at 20.

Figure 5:
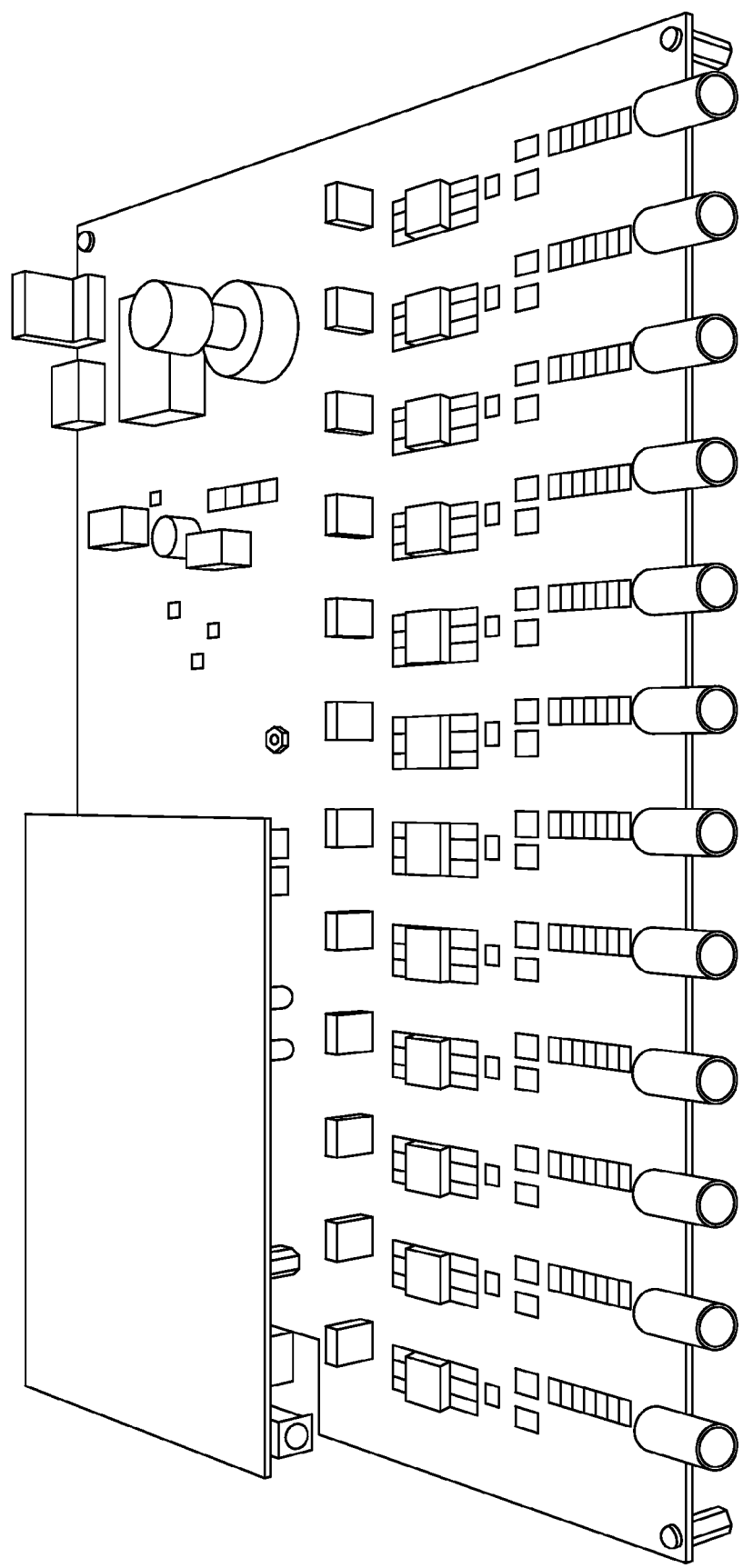
FIG. 5 shows the electronic circuit board with FPGA control hardware.

An embodiment of the electronic circuitry to drive the sensor is shown in FIG. 5. It is comprised of an FPGA (field programmable gate array) board that allowed programmable pulsing and time-phase shifting of voltages to within an accuracy of less than one nanosecond. The FPGA board was connected to a computer running software to interface to the FPGA board and input user values, such as the desired focus and estimated acoustic velocity, the latter which was obtained from a database of values derived from the open literature or from previous knowledge, well known to those skilled in the art.

Figure 6:
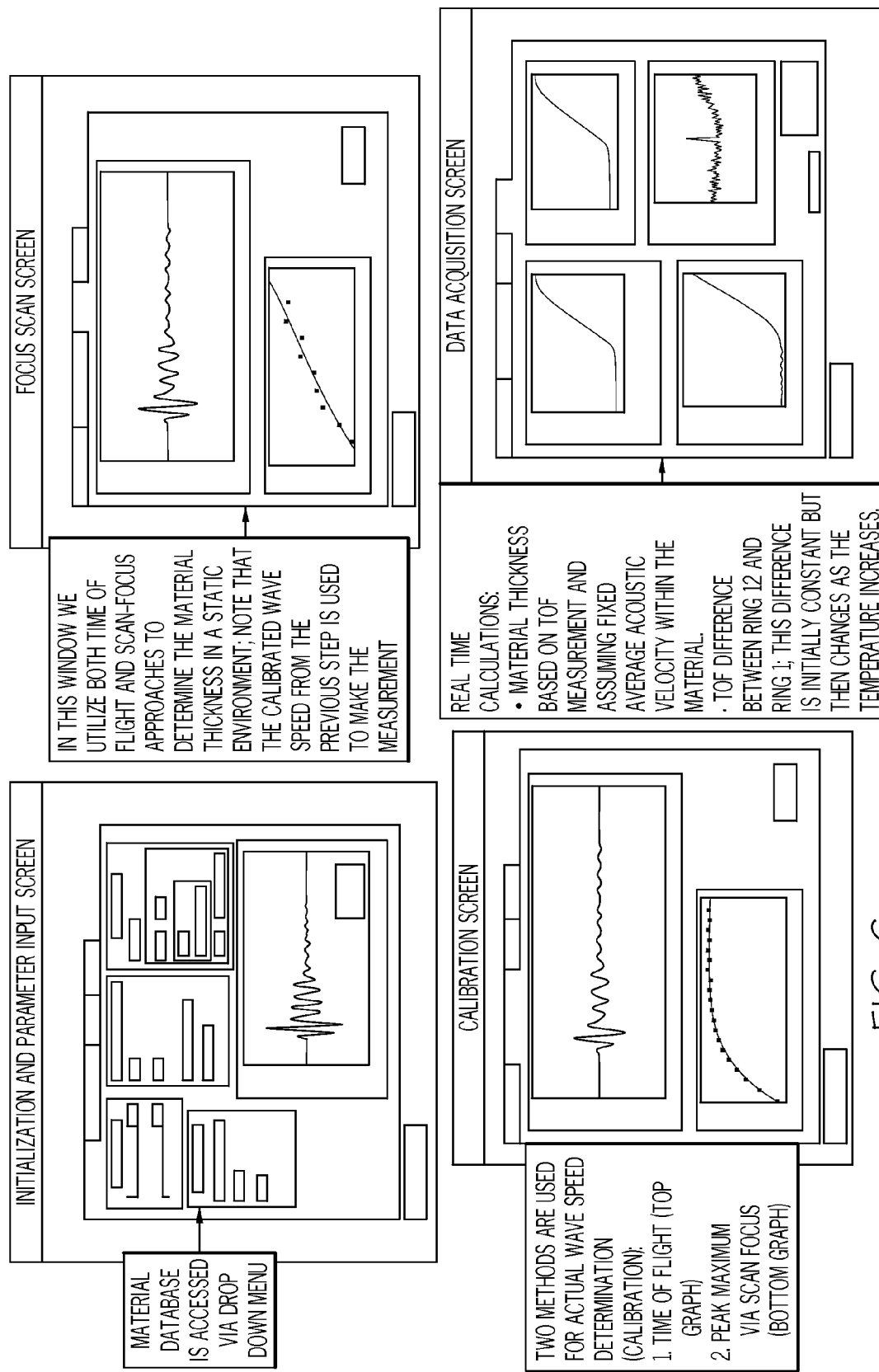
FIG. 6 shows screenshots of the Graphical User Interface (GUI).

Sample user interface screenshots are shown in FIG. 6, which show how the user inputs parameters (Initialization and Parameter Input Screen); performs wave speed calibration (Wavespeed calibration screen); determine the material thickness (Focus Scan Screen), and acquire data (Data Acquisition Screen).

Figure 7:
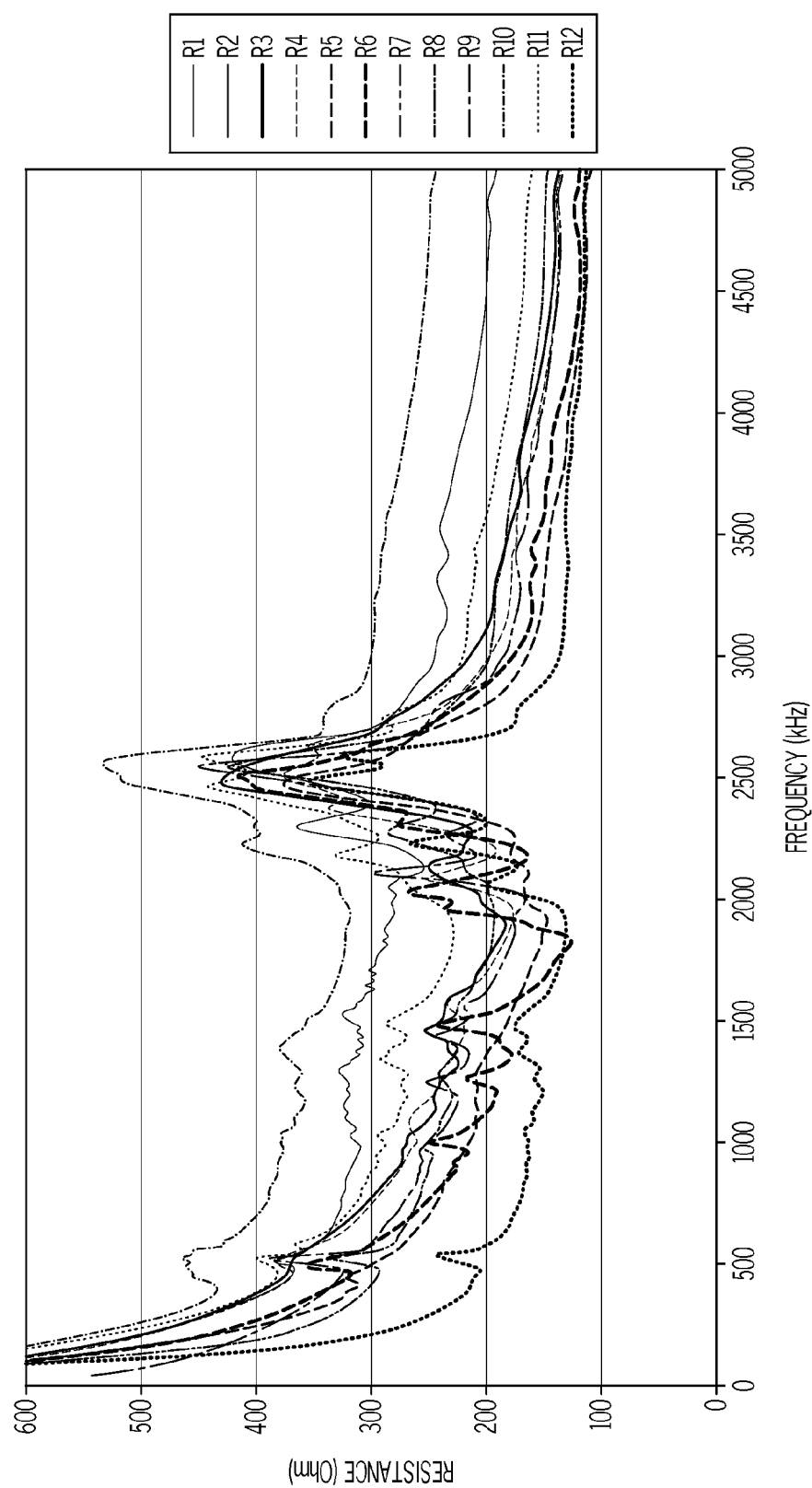
FIG. 7 is a graph of ring impedance measurements exhibiting good resonance at 2.5 MHz.

Preliminary checkouts of the circuitry and the piezoelectric rings was initially performed. Impedance matching showed that all the rings 10 responded well, with resonance at a frequency of 2.5 MHz, as seen in FIG. 7. Further checkouts were performed using a 1.75 inch (44.45 mm) thick lexan block. The setup is shown in FIG. 8.

Figure 8:
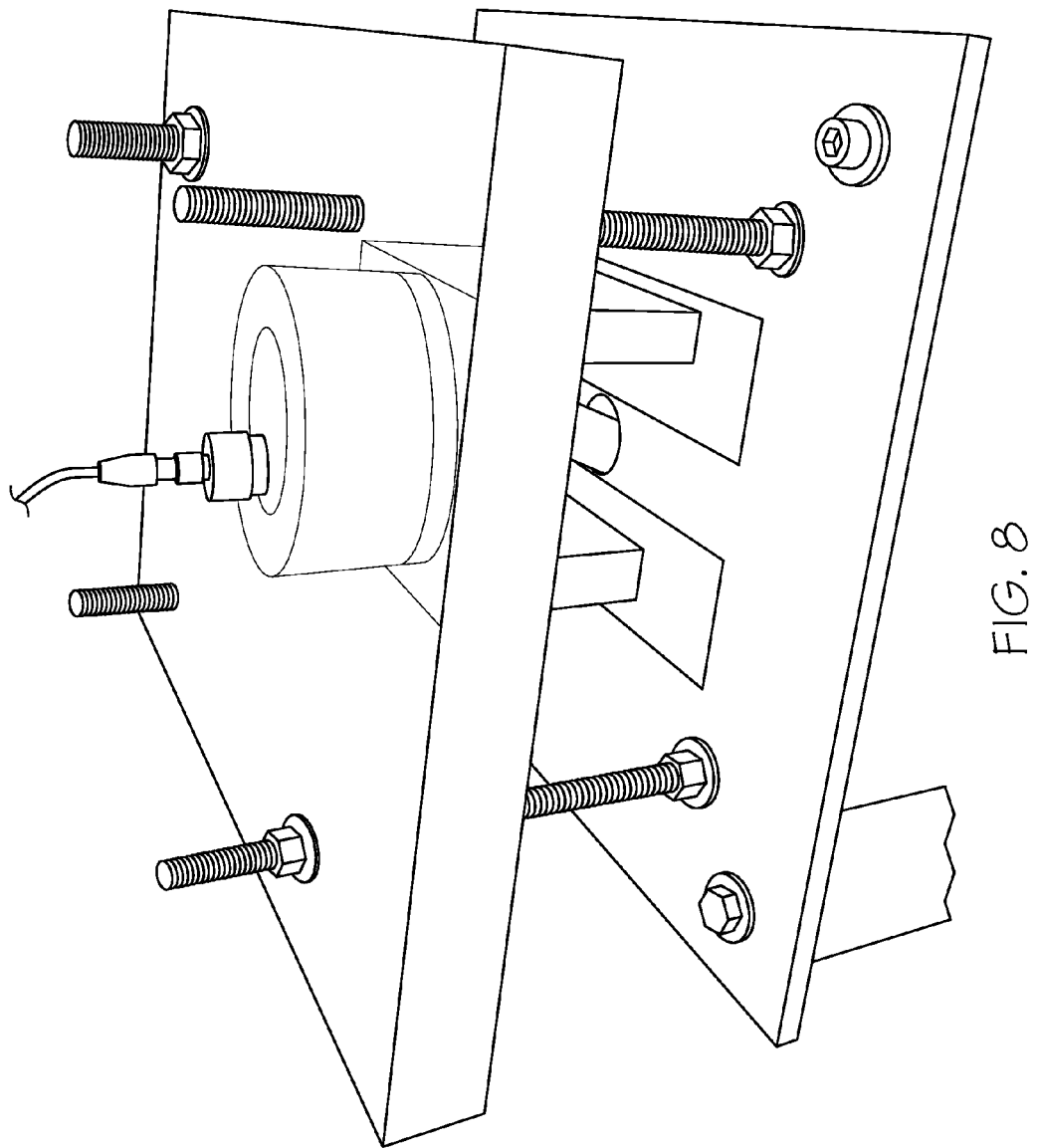
FIG. 8 shows the invention with sensor attached to a Lexan block.
Figure 9:
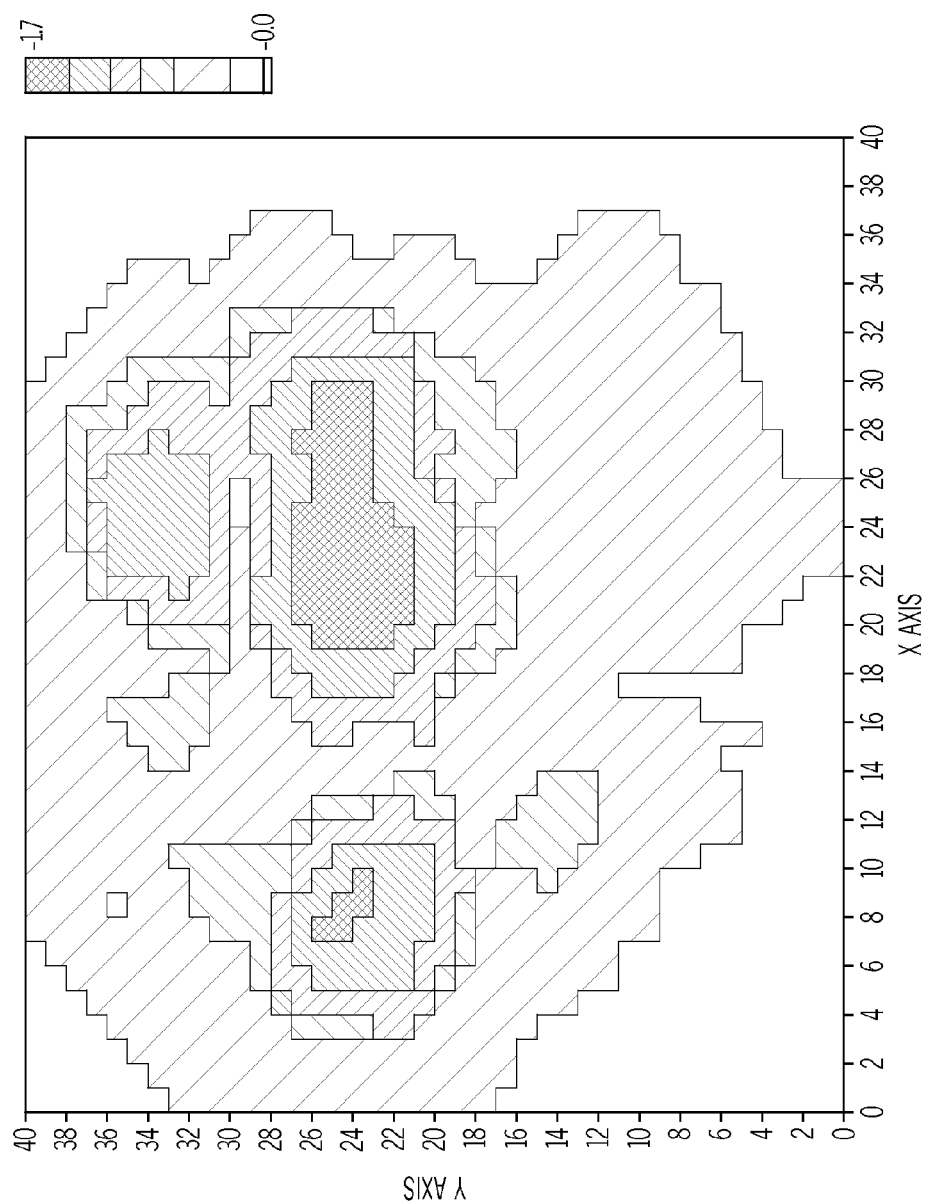
FIG. 9 shows the acoustic pressure distribution measured at the top of the Lexan block with the sensor focused at the interface location (maximum pressure observed at the center of the field; other lateral concentrations are due to noise arising from interference waves produced by cuts in the wear plate that we done to accommodate the electrodes—these would not be there normally).

As seen in FIG. 8, the sensor was mounted below a Lexan block, and initially an equivalent microphone as the one integrated in the sensor was used to map out the acoustic focusing characteristics. A two-dimensional scan was performed with the sensor operating such that the focus of the waves was at the top interface of the Lexan. The results of this scan are shown in FIG. 9. FIG. 9 demonstrates that focus was achieved, but also revealed several less intense side lobes. These lobes were due to cuts in the quartz wear plate that were made to accommodate the electrical wiring from the rings to the connectors. Another embodiment will eliminate the cuts, to eliminate the side lobes and thus generate a cleaner acoustic pressure signal. Regardless, the sensor performance when using the integrated microphone in the pitch and catch mode of the reflected signal was expected to not be affected by the side lobes since the microphone had a directional sensitivity of 7 degrees total angle.

Figure 10:
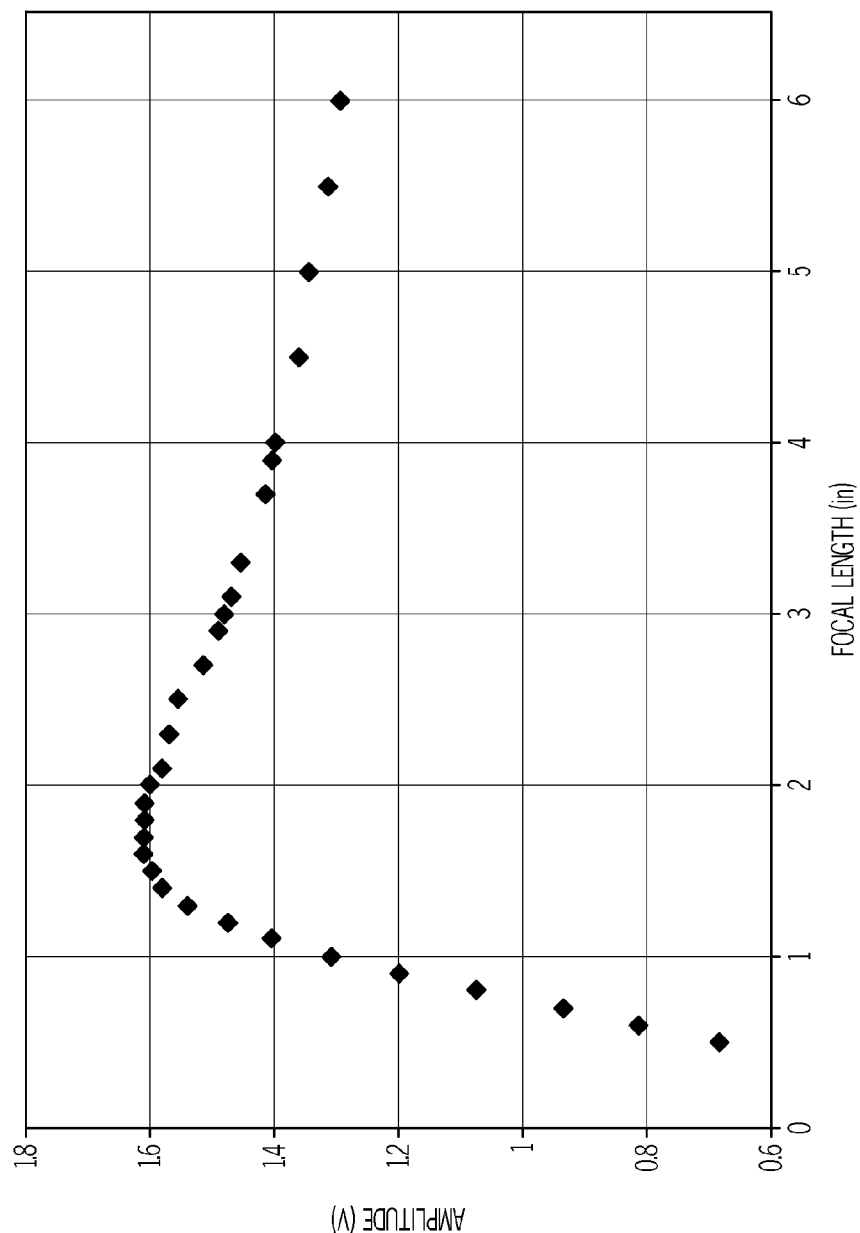
FIG. 10 is a graph of measured intensity of scattered echo during scan-focus procedure through a 1.7 inch thick Lexan.

Lexan was chosen as the baseline material to conduct these checkouts since it offered well known acoustic properties. Inputting the value of the acoustic velocity found in the literature and running the sensor in the scan-focus mode (see FIG. 6) with the waves reflecting off the top interface and focusing back at the center microphone, yielded the response curve shown in FIG. 10. The results demonstrated that as the focus of the device was scanned through a range of values, peak intensity occurred when focal length was matched with the top interface of the Lexan, as expected. Note that in the figure, the focal length is not the true focal length of the waves, but rather half. The response curve is very clean, and local peak fitting around the maximum location yielded the interface location relative to the sensor to within sub-millimeter resolution.

Figure 11:
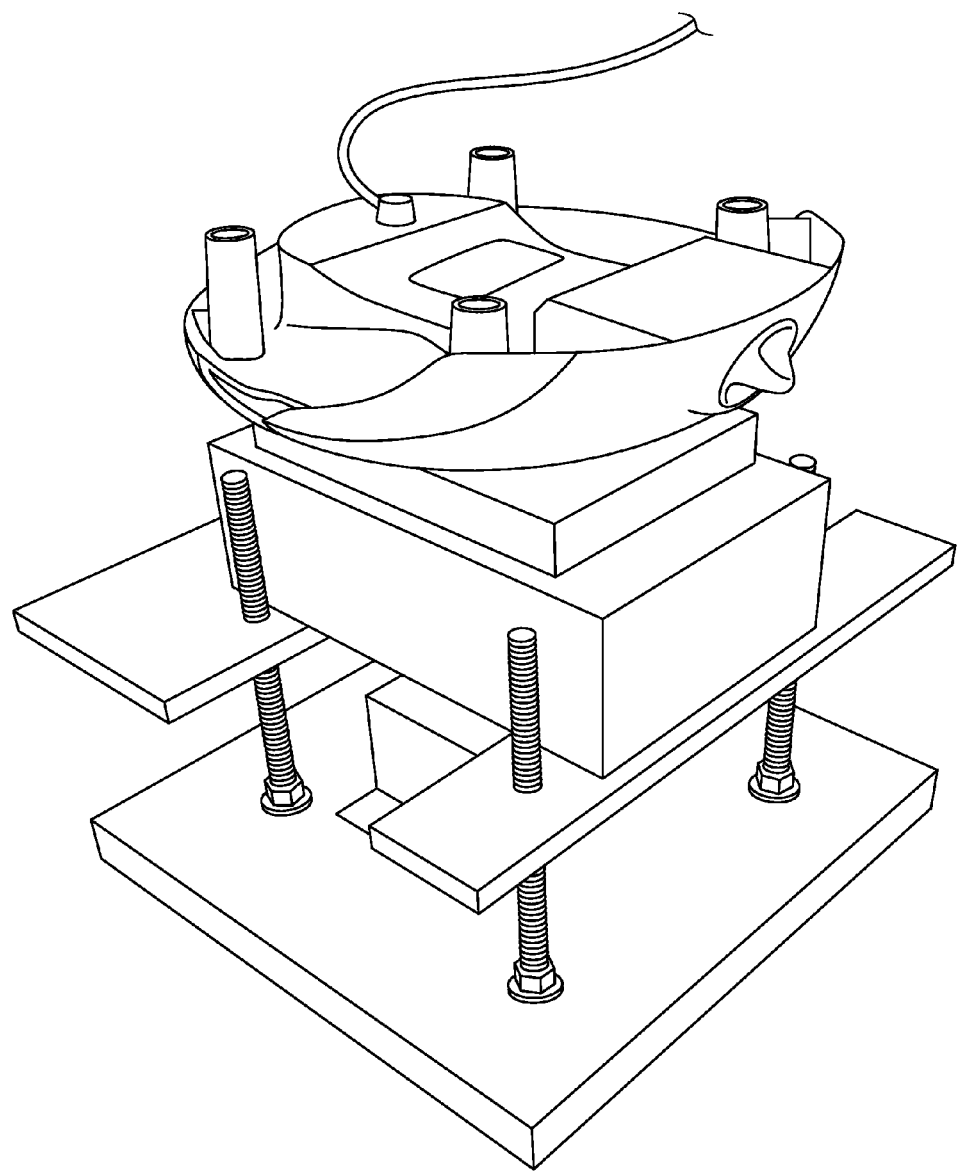
FIG. 11 shows static testing with ablative material and heat addition.
Figure 12:
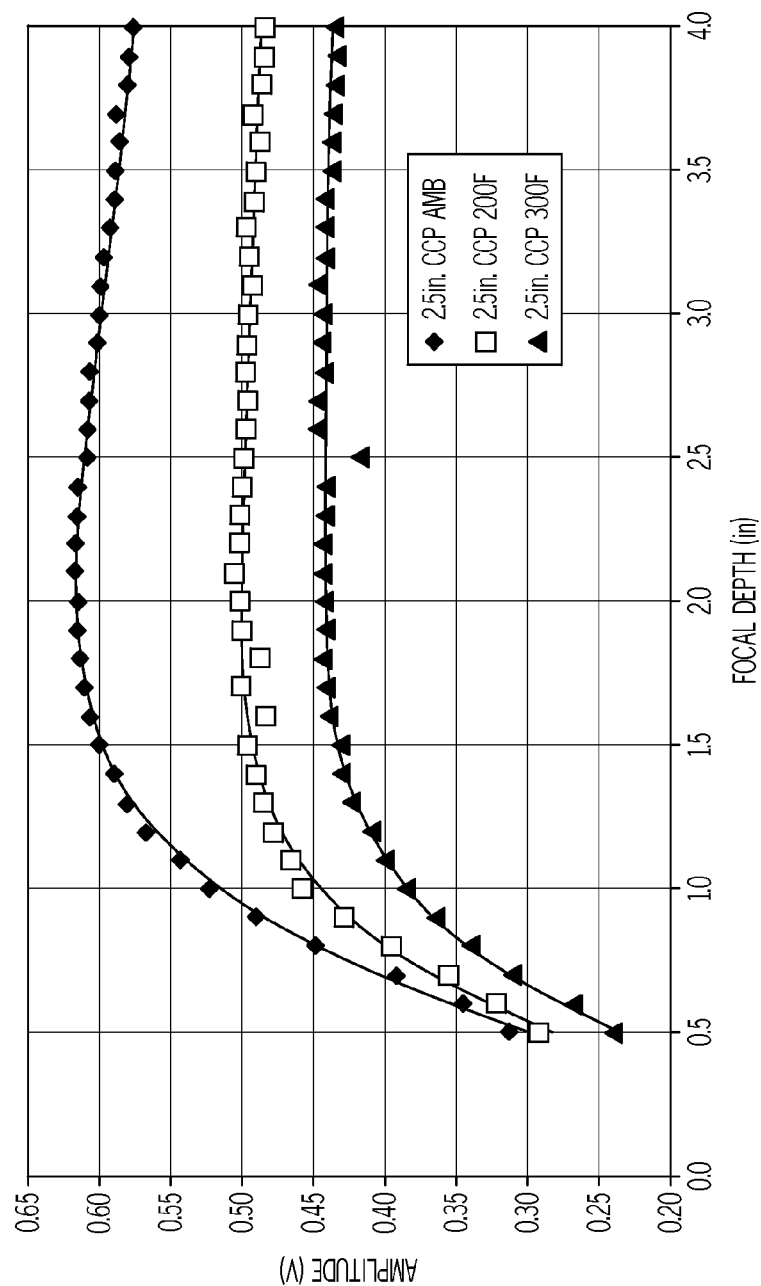
FIG. 12 is a graph of microphone intensity response curves for ablative material under ambient and heated conditions.

Testing with the Lexan material sample demonstrated that the interface location may be accurately found via the scan-focus method. A carbon phenolic ablative material was then tested with the sensor, with heat applied on the top side. The setup for this test is shown in FIG. 11. The sensor was placed on the underside of a 2.5 inch (63.5 mm) thick ablative material. A heat plate with an aluminum block acting as a heat spreader was placed on the top side of the ablative material. Thermocouples on both the top and bottom (sensor) sides of the ablative material were placed to record surface temperatures. Response curves for ambient and two other surface temperatures are shown in FIG. 12. An acoustic velocity value that is average for the material was used, however it was observed from the ambient scan-focus results at this value were not correct. Ablative materials are typically non-isotropic, and the acoustic velocity can vary over a significant range. Therefore, as part of the application process and integrated in the software, a module was incorporated to do an initial setup of the sensor to determine the average acoustic velocity within the material in the orientation that is being sensed, in the sensor itself, by iterating on the value until the peak matches the material thickness as measured by a ruler or a gage (see FIG. 6 where a screenshot of the calibration GUI was shown).

As heat was applied to the CCP ablative in FIG. 12, the response curve amplitude and shape changed from the ambient condition, due to acoustic velocity variation and its effect on the focusing of the twelve individual waves. The change was quite significant, and demonstrated the signal's degradation due to the out-of-phasing of the acoustic waves. Electronic tuning of the phase shift for the PZT rings 10 brings the response curve back to its original form as depicted by the blue line (ambient conditions), thus countering the bias introduced by heating. These test results demonstrated the ability of the inventive sensor to compensate for acoustic velocity biasing due to temperature.

The development of a new non-intrusive sensor for tracking the recession rate of ablative materials with realtime compensation of temperature is shown. An embodiment of the sensor system was designed and built, and preliminary static testing of the device with baseline material demonstrated the proof-of-concept. Additional testing with an ablative material and with heat addition show that the acoustic response curve generated from the focused waves reflecting from the top surface interface changed significantly with temperature, thus demonstrating that significant finesse exists to be able to perform real-time tuning of the time-phase parameters and yield the acoustic velocity distribution curve.

The development of a new sensor for in-situ non-intrusive measurements of recession rate of heat shield ablative materials is described. The sensor utilizes a focused ultrasound approach to non-intrusively detect the ablative material's surface loss while simultaneously correcting for acoustic velocity dependencies on temperature. The latter correction is done via a closed loop feedback approach that yields the average acoustic velocity through the ablative material. The multi-source focusing approach is atypical of current ultrasound based sensors used for ablation recession rate measurement, which require a-priori knowledge of temperature distribution within the ablative to yield accurate data on recession rate. The invention provides unique operational aspects and possibilities as a heat shield health monitoring system for future spacecraft.

Figure 13B:
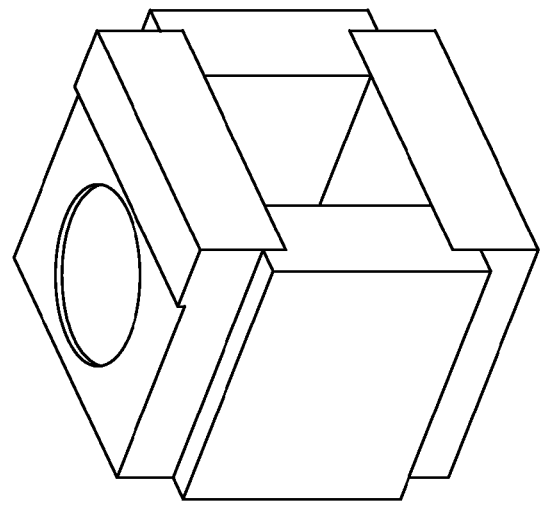
FIG. 13 is a schematic showing sensor mounted on the outside of the test sample comprised of carbon phenolic material to be tested under high heat and high shear flow.
Figure 13A:
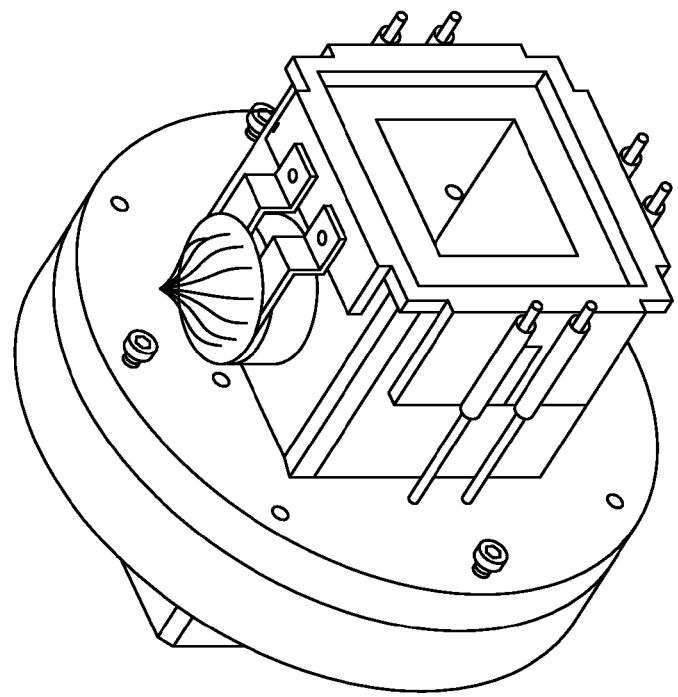
Figure 14:
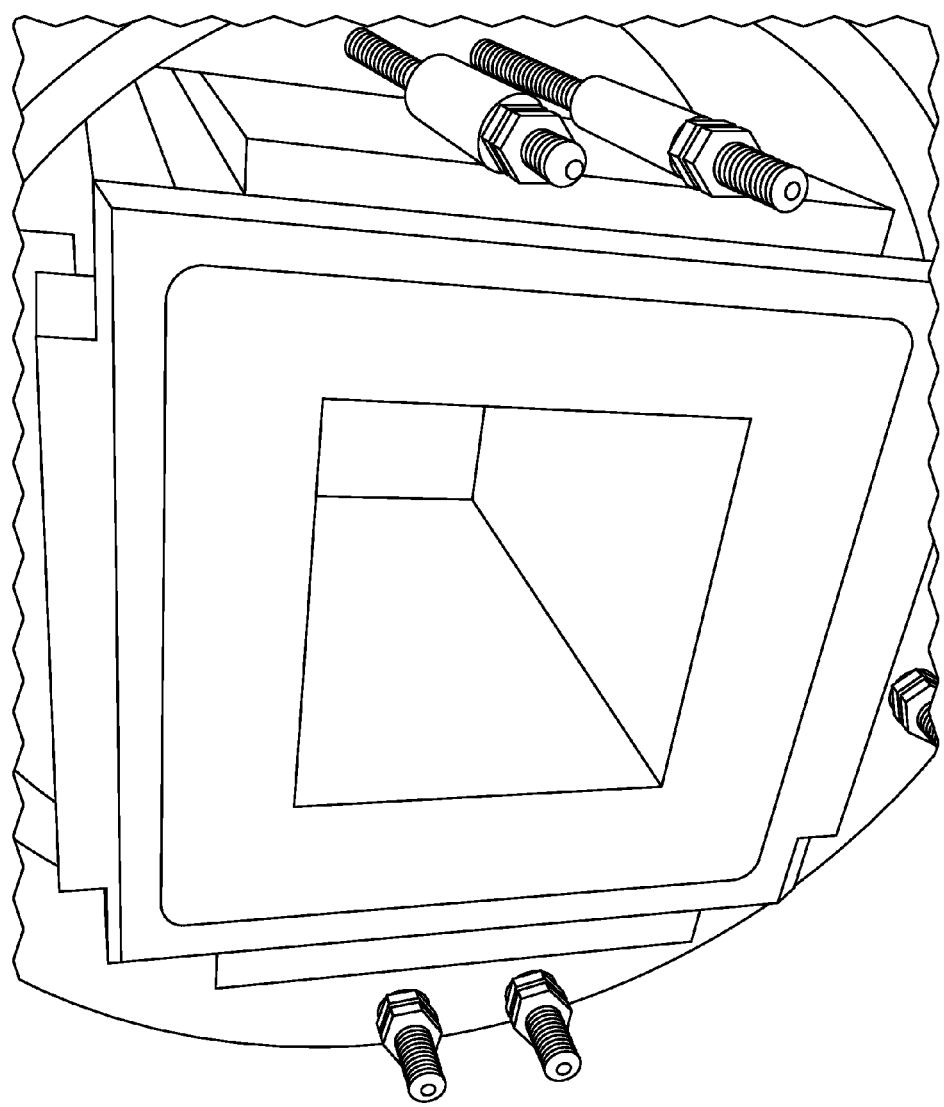
FIG. 14 shows the carbon phenolic material post test showing final material recession.
Figure 15:
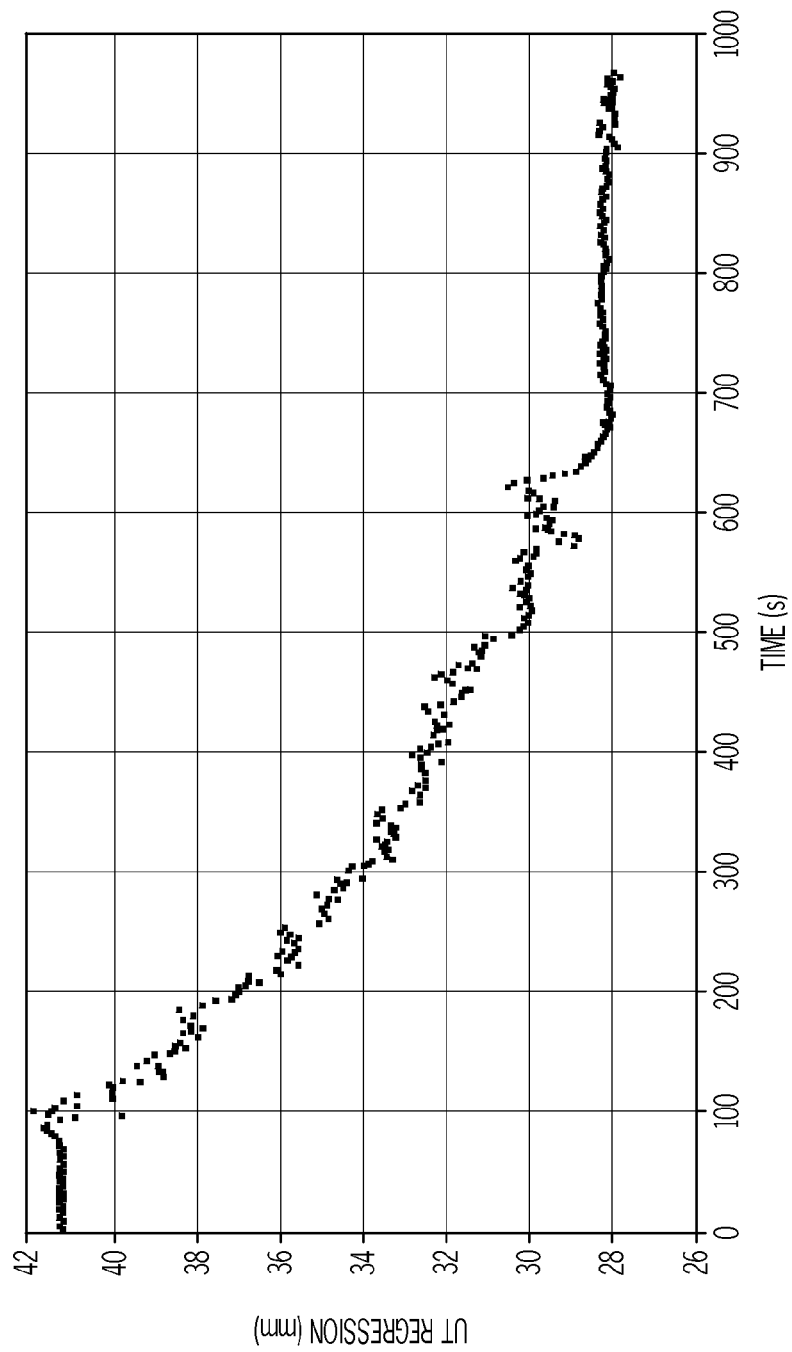
FIG. 15 is a measurement of the ablative material receding obtained by the in-situ sensor during the hot test.

FIG. 13 shows the sensor being applied during for measuring the recession rate of carbon phenolic material under high shear and high temperature test conditions. A view of the material sample post test is shown in FIG. 14. Post processed measurements of the amount of virgin material by the in-situ sensor are shown in FIG. 15, demonstrating the ability of the sensor to track the interface location during a dynamic event. The recession rate is the then the derivative of the data shown in FIG. 15. While this data was obtained post analysis of the raw signals, it is envisioned that real-time processing of the raw data and application of the feedback mechanism as part of the scan-focus approach will yield real time tracking data of the recession surface location, and therefore its recession rate.

Figure 16:
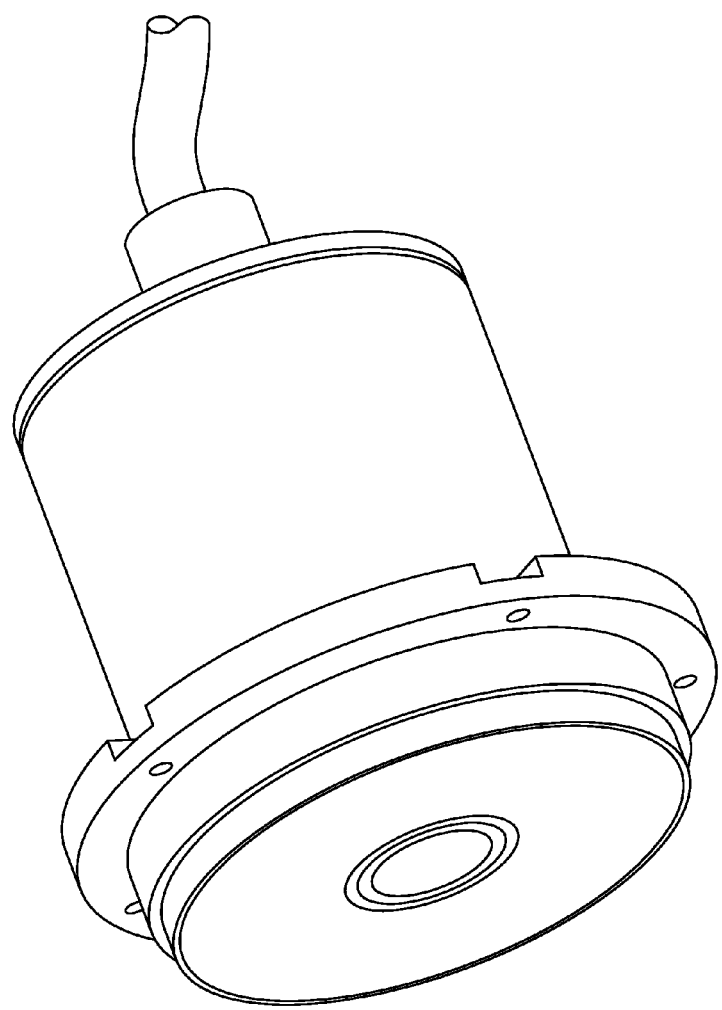
FIG. 16 is another embodiment of the inventive sensor in which sensor head features 6 resonator rings tuned for 250 kHz, segregated microphone in the middle with dual aperture capability and external aluminum can, to house entire assembly.

FIG. 16 shows another embodiment of the acoustic sensor for recession rate measurement. This embodiment has been designed for operation at 250 kHz to be used for highly porous ablative materials, such as PICA. Due to size constraints it features 6 resonator rings and a custom center microphone that has a dual aperture. The PZT rings for the sensor and the microphone lie behind a wear plate that is of dual material layers to optimize coupling of the acoustic signal into low capacitance materials such as PICA.

The dual or multiple aperture approach at the microphone gives the sensor the added capability of distinguishing if the recession or erosion at the local area of measurement is non-laminate in nature, i.e. non-planar local surface erosion. This is done by performing a cross-correlation of the two or more aperture signals to determine departures from baseline (very strong correlation, or very weak correlation). The dual or multiple aperture approach takes advantage of spatial filtering and the fact that waves arrive at different times over the whole surface of the microphone, and thus any non-planar erosion will change the spatial distribution of waves in comparison to the ideal flat reflecting surface scenario.

What is claimed is:

1. A non-intrusive sensor for in-situ measurement of recession rate of ablative and eroding materials, comprising:
    a housing, which is mounted near an ablative material for which the recession rate is to be monitored;
    an ultrasonic wave source carried in the housing;
    a microphone, carried in the housing, for collecting the reflected ultrasonic waves from an interface surface of the ablative or eroding material;
    a time phasing control circuit for time-phasing the ultrasonic wave source so that the waves reflected from the interface surface of the ablative material focus on the microphone, to maximize the acoustic pressure detected by the microphone, and
    a circuit for computing the location off of which the ultrasonic waves scattered to focus back at the microphone, whereby the recession rate of the heat shield ablative is monitored in real-time.

2. The non-intrusive sensor for in-situ measurement of recession rate of ablatives and eroding materials of claim 1 wherein the ultrasonic wave source is comprised of an annular concentric array of a plurality of piezoelectric ring resonators.

3. The non-intrusive sensor for in-situ measurement of recession rate of ablatives and eroding materials of claim 2 wherein the microphone, having at least one aperture, is arranged at the center of the concentric array of the plurality of piezoelectric ring resonators.

4. The non-intrusive sensor for in-situ measurement of recession rate ablatives and other eroding materials of claim 3 wherein the microphone has a frequency response curve optimized for the resonating frequency of the piezoelectric rings.

5. The non-intrusive sensor for in-situ measurement of recession rate ablatives and eroding materials of claim 2 wherein the plurality of piezoelectric ring resonators is comprised of 6 piezoelectric rings.

6. The non-intrusive sensor for in-situ measurement of recession rate of ablatives and other eroding materials of claim 5 wherein the response curve of each ring is maximized by real-time time-shift tuning, such that the sensor autocompensates for temperature effects on the ablative material being real-time monitored.

7. The non-intrusive sensor for in-situ measurement of recession rate ablatives and eroding materials of claim 2 wherein the plurality of piezoelectric ring resonators is comprised of 12 piezoelectric rings.

8. The non-intrusive sensor for in-situ measurement of recession rate ablatives and other eroding materials of claim 2 wherein the plurality of piezoelectric ring resonators each have a predetermined width, and wherein the rings are spaced apart from each other.

9. The non-intrusive sensor for in-situ measurement of recession rate of heat shield ablatives of claim 8 wherein the predetermined width is 0.020 inches.

10. The non-intrusive sensor for in-situ measurement of recession rate ablatives and other eroding materials of claim 2 wherein the plurality of piezoelectric ring resonators each have a predetermined width, and wherein the rings are spaced apart from each other, the width of each ring being selected so that the surface area of each ring is the same.

11. The non-intrusive sensor for in-situ measurement of recession rate ablatives and other eroding materials of claim 2 wherein the plurality of piezoelectric ring resonators each have a predetermined width, and wherein the rings are spaced apart from each other so as to minimize cross-talk, to isolate each ring from the other rings.

12. The non-intrusive sensor for in-situ measurement of recession rate of ablatives and other eroding materials of claim 2 wherein the plurality of piezoelectric ring resonators each have the same predetermined width, and wherein the rings are spaced apart from each by the predetermined width.

13. The non-intrusive sensor for in-situ measurement of recession rate of ablatives and other eroding materials of claim 2 wherein the plurality of piezoelectric ring resonators are mounted on a substrate material that can serve as electrical ground if electrically conductive, and including filler material to mitigate against back resonance.

14. The non-intrusive sensor for in-situ measurement of recession rate of ablatives and other eroding materials of claim 13 wherein insulated wires bonded to the opposite end of each ring with respect to the substrate serving as common ground, which were conductively connected to the time-phasing control circuit.

15. The non-intrusive sensor for in-situ measurement of recession rate of ablatives and other eroding materials of claim 14 further including a wear plate connected to the housing on top of the array of rings, to seal the piezoelectric rings from the environment, the wear plate having an opening corresponding to the location of the microphone, and whereas the wear plate can be comprised of single or multi-layer construction, made of a variety of common materials, optimized to coupling the acoustic signal into the ablative material of interest.

16. The non-intrusive sensor for in-situ measurement of recession rate of ablatives and other eroding materials of claim 1, wherein the sensor may be surface mounted for directing the ultrasonic waves generated by the ultrasonic wave source toward the ablative material for which the recession rate is to be measured.

17. The non-intrusive sensor for in-situ measurement of recession rate of ablatives and other eroding materials of claim 16 wherein the sensor is surface mounted near, but not in direct contact with the ablative material to be monitored, given that acoustic waves can propagate through the added material and into the ablative material of interest with minimum loss.

18. The non-intrusive sensor of claim 1 wherein the microphone has dual apertures, the dual apertures permitting cross-correlation of the dual aperture signals to determine departures from a baseline, which allows for distinguishing if the recession or erosion at the local area of measurement is non-laminate in nature.

19. The non-intrusive sensor of claim 1 further including real-time feedback control, which combines signal processing and dynamic time-shifting to perform scan-focus and track the interface, the algorithm for acoustic velocity compensation is:

$$\left\{\begin{array}{c} t_1 + \delta\tau_1 \\ t_2 + \delta\tau_2 \\ \vdots \\ t_{N-1} + \delta\tau_{N-1} \\ t_N + \delta\tau_N \end{array}\right\}^{(s-1)} + \left\{\begin{array}{c} \varepsilon\tau_1 \\ \varepsilon\tau_2 \\ \vdots \\ \varepsilon\tau_{N-1} \\ \varepsilon\tau_N \end{array}\right\}^{(s)} =$$

$$\frac{1}{N}\left\{\begin{array}{c} D_1 \\ D_2 \\ \vdots \\ \varepsilon\tau_{N-1} \\ \varepsilon\tau_N \end{array}\right\}^{(s-1)} \otimes \left\{\frac{1}{C_1} \quad \frac{1}{C_2} \quad \cdots \quad \frac{1}{C_{N-1}} \quad \frac{1}{C_N}\right\}^{(s)} =$$

$$\left\{\begin{array}{c} D_1 \\ D_2 \\ \vdots \\ D_{N-1} \\ D_N \end{array}\right\}^{(s-1)} \cdot \frac{1}{C_{avg}^{(s)}}.$$

* * * * *